United States Patent [19]

Denny et al.

[11] Patent Number: 5,281,620
[45] Date of Patent: Jan. 25, 1994

[54] COMPOUNDS HAVING ANTITUMOR AND ANTIBACTERIAL PROPERTIES

[75] Inventors: William A. Denny; Bruce C. Baguley; Graham J. Atwell; Gordon W. Rewcastle, all of Auckland, New Zealand

[73] Assignee: Cancer Research Campaign Technology Limited, London, England

[21] Appl. No.: 912,466

[22] Filed: Jul. 13, 1992

Related U.S. Application Data

[63] Continuation of Ser. No. 793,506, Nov. 15, 1991, abandoned, which is a continuation of Ser. No. 554,974, Jul. 16, 1990, abandoned, which is a continuation of Ser. No. 137,271, Dec. 23, 1987, abandoned.

[30] Foreign Application Priority Data

Dec. 23, 1986 [NZ] New Zealand ................. 218781

[51] Int. Cl.$^5$ ............... A61K 31/335; C07D 311/78
[52] U.S. Cl. .................................. 514/455; 549/392
[58] Field of Search .................. 549/392; 514/455

[56] References Cited

PUBLICATIONS

Nakanishi et al., Chem Abstr., 76: 126,784w (1972). (Abstract of Japan 7200425).
Nishino et al., Bull. Chem. Soc. Jpn., 56, 2847–48 (1983).
Nishino et al., ibid., 56, 474–480 (1983).

Primary Examiner—Nicky Chan
Attorney, Agent, or Firm—Pennie & Edmonds

[57] ABSTRACT

The novel class of xanthenone-4-acetic acids represented by the general formula (I)

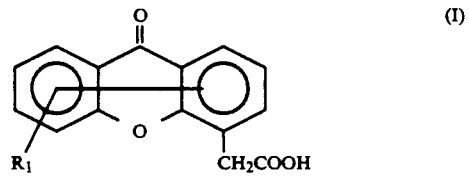

where $R_1$ represents up to two of the groups lower alkyl, halogen, $CF_3$, CN, $NO_2$, $NH_2$, $CH_2COOH$, $OR_2$, OH, $NHCOR_2$, $NHSO_2R_2$, $SR_2$, $SO_2R_2$, $CH_2CONHR_2$ or $NHR_2$ (where $R_2$ is lower alkyl optionally substituted with hydroxy, amino or methoxy functions), at any of the positions 1–8 which are available, $R_1$ may also represent the substitution of an aza (—N=) group for one or two of the methine (—CH=) groups in the carbocyclic rings and two of $R_1$ on any two available adjacent positions may also represent the grouping —CH=CH—CH=CH— to form an additional fused benzene ring; and basic addition salts thereof, possess antitumour and antibacterial properties.

6 Claims, No Drawings

COMPOUNDS HAVING ANTITUMOR AND ANTIBACTERIAL PROPERTIES

This is a continuation of application Ser. No. 07/793,506, filed Nov. 15, 1991, abandoned, which is a continuation of application Ser. No. 07/554,974, filed Jul. 16, 1990, abandoned, which is a continuation of application Ser. No. 137,271, filed Dec. 23, 1987, abandoned.

BACKGROUND OF THE INVENTION

Xanthenone-1-acetic acid has been prepared previously (H. Nichino and K. Kurosawa, *Bull. Soc. Chem. Jap.*, 1983, 56, 2847), and has been evaluated as an anti-inflammatory agent (M. Nakanishi, T. Oe, M. Tsuruda, H. Matsuo, S. Sukuragi, Y. Maruyama, *Yakugaki Zasshi*, 1976, 96, 99; Chem. Abstr. 1976, 84, 135515b). Xanthenone-2-acetic acid has also been reported previously (M. Henryk, *Pol. J. Chem.*, 1980, 54, 2059) and has been evaluated as an anti-inflammatory agent (M. Nakanishi, T. Oe, Y. Maruyama, Ger. Offen. 2,015,265; Chem. Abstr. 74P, 13008m: M. Nakanishi, T. Oe, S. Kakuragi, Japan 73 26 767; Chem. Abstr. 78P, 159430x). Xanthenone-4-acetic acid has been prepared previously (H. Nishino and K. Kurosawa, *Bull. Soc. Chem. Jap.*, 1983, 56, 2847), and has been evaluated as an anti-inflammatory agent (M. Nakanishi, T. Oe, M. Tsurada, H. Matsuo, S. Sakuragi, Y. Maruyama, *Yakugaku Zasshi*, 1976, 96, 99; Chem. Abstr. 1976, 84, 135515b; M. Nakanishi, T. Oe, Y. Manuyama, Japan 72 00 425; Chem. Abstr. 1972, 76P, 126784e).

SUMMARY OF THE INVENTION

The present invention relates to novel xanthenone-4-acetic acids having antitumour and antibacterial properties, to methods of preparing the novel compounds, and to the use of these compounds as antitumour and antibacterial agents.

We have now found that xanthenone-4-acetic acids falling within the scope of formula (I) hereinafter have antibacterial and antitumour properties and are useful as antibacterial and antitumour agents.

DESCRIPTION OF THE INVENTION

The novel class of xanthenone-4-acetic acids of the present invention is represented by the general formula (I)

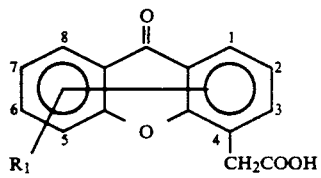

where $R_1$ represents up to two of the groups: lower alkyl, phenyl halogen, $CF_3$, $CN$, $NO_2$, $NH_2$, $CH_2COOH$, $OR_2$, $OH$, $NHCOR_2$, $NHSO_2R_2$, $SR_2$, $SO_2R_2$, $CH_2CONHR_2$ or $NHR_2$ (where $R_2$ is lower alkyl optionally substituted with hydroxy, amino or methoxy functions), at any of the positions 1–8 which are available, $R_1$ may also represent the substitution of an aza (—N=) group for one or two of the methine (—CH=) groups in the carbocyclic rings and two of $R_1$ on any two available adjacent positions may also represent the grouping —CH=CH—CH=CH— to form an additional fused benzene ring; and basic addition salts thereof. When either $R_1$ or $R_2$ represents lower alkyl, the group may contain from 1 to 5 carbon atoms.

The compounds of formula (I) form pharmaceutically acceptable salts with both organic and inorganic bases. Examples of suitable bases for salt formation include alkali metal hydroxides and carbonates, ammonia and lower alkylamines where the alkyl group may be optionally substituted with hydroxy groups.

The xanthenone-4-acetic acids of general formula (I) and the salts thereof may be prepared by a process which comprises cyclodehydrating a substituted phenoxybenzoic acid of the general formula (IV)

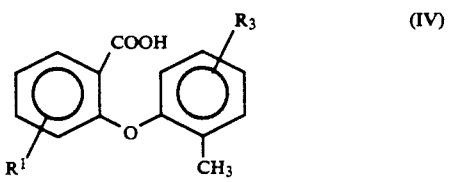

where $R_1$ is hydrogen or is $R_1$ as defined for formula (I) and $R_3$ is as defined for $R_1$, not more than one of $R_1$ and $R_3$ being hydrogen; brominating the obtained 4-methylxanthenone of the general formula (VI)

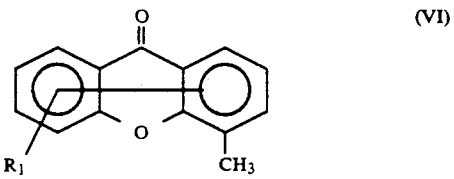

reacting the obtained 4-bromomethylxanthenone of the general formula (VII)

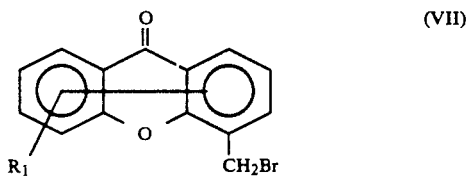

with an inorganic cyanide, and hydrolysing the obtained xanthenone-4-acetonitrile of the general formula (VIII)

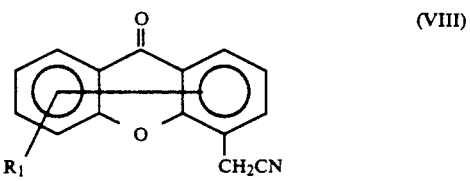

to the corresponding compound of formula (I) and, if desired, converting the compound of formula (I) to a basic addition salt thereof.

The compounds of general formula (I) and the salts thereof may be more directly prepared by a process which comprises cyclodehydrating a substituted phenoxyphenylacetic acid of the general formula (XI)

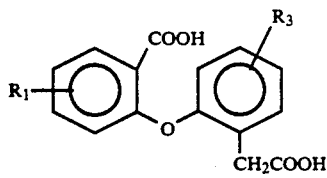
(XI)

where $R_1$ is hydrogen or is $R_1$ as defined for formula (I) and $R_3$ is as defined for $R_1$, not more than one of $R_1$ and $R_3$ being hydrogen, to the corresponding compound of formula (I) and, if desired, converting the compound of formula (I) into a basic addition salt thereof.

The xanthenone-4-acetic acids of general formula (I) and the salts thereof may further be prepared by a process which comprises cyclodehydrating a compound of the general formula (XVIII)

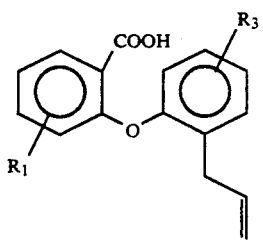
(XVIII)

where $R_1$ is hydrogen or is $R_1$ as defined for formula (I) and $R_3$ is as defined for $R_1$, not more than one of $R_1$ and $R_3$ being hydrogen; oxidising the obtained 4-allylxanthenone of the general formula (XIX)

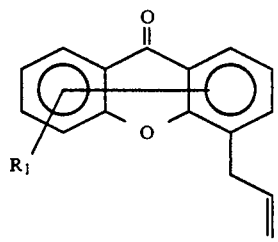
(XIX)

to the corresponding compound of formula (I) and, if desired, converting the compound of formula (I) into a basic addition salt thereof.

Compounds of the general formula (I), wherein $R_1$ is in the 5-position, and the salts thereof may be prepared by a process which comprises subjecting a compound of the general formula (XXII)

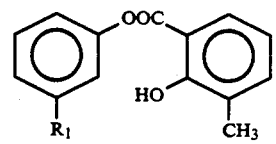
(XXII)

wherein $R_1$ is as defined for formula (I), to controlled pyrolysis, brominating the obtained 4-methylxanthenone of the general formula (XXIII)

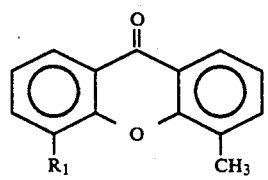
(XXIII)

reacting the obtained 4-bromomethylxanthenone with an inorganic cyanide; and hydrolysing the obtained xanthenone-4-acetonitrile to the corresponding compound of formula (I) and, if desired, converting the compound of formula (I) to a basic addition salt thereof.

The above processes for preparing the compounds of the invention, and the preparation of the respective starting materials, are outlined in the following Schemes I–IV.

SCHEME I

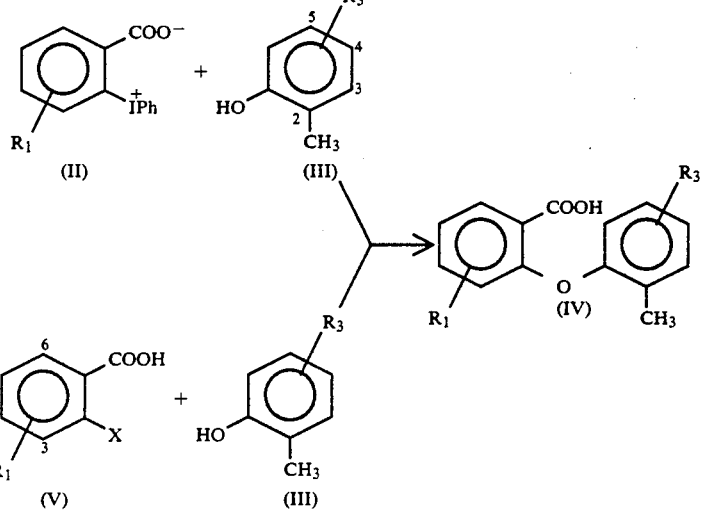

method 1a

SCHEME I
-continued (VI): Z = CH₃
(VII): Z = CH₂Br
(VIII): Z = CH₂CN method 1b (I)

SCHEME II method 2a (V) + (X) →

(XI)

method 2b (XII) → →

(XIII): Z = OH
(XIV): Z = halogen
(XV): Z = CN (X)

SCHEME III (V) + (XVII) →

(XVIII) →

(XIX) → compounds of formula (I)

SCHEME IV (XX) + (XXI) →

(XXII) →

(XXIII) → compounds of formula (I)

In Scheme I, $R_1$ is hydrogen or is $R_1$ as defined for formula (I), $R_3$ is as defined for $R_1$, and X is halogen.

Reaction of either diphenyliodonium-2-carboxylates (II) or halobenzoic acids (V) with phenols (III) gives the phenoxybenzoic acids (IV) in moderate yields. Reactions using diphenyliodonium-2-carboxylates (method 1a) are typically carried out at 90°-140° C. for 5-10 hours in either excess phenol as solvent or DMF as cosolvent. Reactions using halobenzoic acids (method 1b) are typically carried out at 100°-180° C. for 5-10 hours, using dipolar aprotic solvent (e.g. DMF, N-methylpyrrolidone, DMSO, HMPT, or preferably anisole or dioxan), together with 10 mole-% of CuCl and 10 mole-% of tris-[2-(2-methoxyethoxy)ethyl]amine (TDA-1, Aldrich Chemical Co).

The phenoxybenzoic acids (IV) are cyclized to the methylxanthones (VI) using a variety of cyclodehydrating conditions (e.g. 90-100% sulfuric acid, methanesulfonic acid, polyphosphoric acid, polyphosphate ester). Free-radical bromination of the methylxanthenones using bromine carriers such as N-bromosuccinimide or N-bromomaleimide and a radical initiator gives the bromomethyl compounds (VII), which undergo substitution reactions with inorganic cyanides to give the acetonitriles (VIII). Hydrolysis of these with aqueous acid then gives the desired xanthenoneacetic acids (I).

In Scheme II, $R_1$ and $R_3$ are as defined above and X is halogen. Reaction of halobenzoic acids (V) with hydroxyphenylacetic acids (X) (method 2a) using the conditions described above for method 1b gives the phenoxyphenylacetic acids (XI) in moderate to good yields, and these can be cyclized by the methods given above to give the desired xanthenone-4-acetic acid (I) directly.

Substituted 2-hydroxyphenylacetic acids (X) are conveniently prepared from available substituted salicylic acids by method 2b.

The substituted salicylic acids are treated with excess benzyl bromide under phase-transfer catalysis (tetrabutylammonium bromide), followed by treatment with alkali to hydrolyse the benzyl ester, to give the O-protected salicylic acids (XII). The corresponding acid chlorides are then made using thionyl chloride, and are reduced with sodium borohydride to the alcohols (XIII). These are converted to the halides (XIV, Z=Cl or Br) by treatment with the appropriate phosphorus trihalide, and then to the acetonitrile (XV) with NaCN under phase-transfer catalysis as above. Alkaline hydrolysis is then used to provide the O-protected acetic acid, which is not purified but deprotected by hydrogenation to give the desired substituted 2-hydroxyphenylacetic acids (X).

In Scheme III, $R_1$ and $R_3$ are as defined above, and X is halogen. Reaction of halobenzoic acids (V) with 2-allylphenols (XVII) using the conditions described above for method 1b gives the ethers (XVIII) in moderate to good yields, and these can be cyclized by the methods given above to give the 4-allylxanthones (XIX). Controlled oxidation of the allyl group using $KMnO_4$ or other oxidants gives the desired xanthenone-4-acetic acids (I).

In Scheme IV, $R_1$ is as defined above for formula (I). Condensation of the appropriate phenol (XX) with 3-methylsalicylic acid (XXI) gives the esters (XXII) which on controlled pyrolysis yield the 4-methylxanthenones (XXIII) in low to moderate yield. These compounds can then be elaborated by the above methods to the compounds of formula (I).

The following Tables I and II set out physical data for compounds within the general formula (I), representative of it, and preparable by the processes of the invention.

TABLE I

Substituted xanthenone-4-acetic acids of Formula (I)

| No | $R_1$ | Mp (°C.) | MW |
|---|---|---|---|
| 1 | H | 214-216 | 254.23 |
| 2 | 1-$CH_3$ | 206-209 | 268.26 |
| 3 | 1-$OCH_3$ | 223-227 | 284.26 |
| 4 | 1-Cl | 205-207 | 288.68 |
| 5 | 2-$CH_3$ | 243-245 | 268.26 |
| 6 | 2-$OCH_3$ | 229-231 | 284.26 |
| 7 | 2-Cl | 272-273 | 288.68 |
| 8 | 3-Cl | 214-218 | 288.68 |
| 9 | 5-$CH_3$ | 206-208 | 268.26 |
| 10 | 5-$CH_2CH_3$ | 210-211 | 282.27 |
| 11 | 5-Ph | 248-249 | 330.32 |
| 12 | 5-$OCH_3$ | 223-224 | 284.26 |
| 13 | 5-$OCH_2CH_3$ | 278-279 | 298.27 |
| 14 | 5-OH | 269-270 | 270.25 |
| 15 | 5-Cl | 238.5-239.5 | 288.68 |
| 16 | 5-$NO_2$ | 244-249 | 299.23 |
| 17 | 5-$NH_2$ | 266-267 | 269.25 |
| 18 | 5-$NHCOCH_3$ | 301-303 | 311.28 |
| 19 | 5-aza | 229-230 | 255.22 |
| 20 | 5-$CH_2COOH$ | 303-305 | 312.27 |
| 21 | 5-$CH_2CONHCH_3$ | 267-269 | 325.29 |
| 22 | 6-$CH_3$ | 224-225 | 268.26 |
| 23 | 6-$OCH_3$ | 205-207 | 284.26 |
| 24 | 6-OH | 303-305 | 270.25 |
| 25 | 6-Cl | 248-249 | 288.68 |
| 26 | 7-$CH_3$ | 209-212 | 268.26 |
| 27 | 7-$OCH_3$ | 220-221 | 284.26 |
| 28 | 7-OH | 233-235 | 270.25 |
| 29 | 7-Cl | 195-199 | 288.68 |
| 30 | 7-$NO_2$ | 274-276 | 299.23 |
| 31 | 8-$CH_3$ | 198-201 | 268.26 |
| 32 | 8-$OCH_3$ | 223-225 | 284.26 |
| 33 | 8-Cl | 205-207 | 288.68 |
| 34 | 5,6-di$CH_3$ | 259-261 | 282.45 |
| 35 | 5,6-benz | 282-284 | 304.31 |
| 36 | 6,7-benz | 275-278 | 304.31 |

TABLE II

Elemental Analyses for the compounds of Table I

| No | Formula | Found C | H | N | Cl | Calculated C | H | N | Cl |
|---|---|---|---|---|---|---|---|---|---|
| 1 | $C_{15}H_{10}O_4$ | 71.0 | 3.9 | | | 70.9 | 4.0 | | |
| 2 | $C_{16}H_{12}O_4$ | 71.2 | 4.5 | | | 71.6 | 4.5 | | |
| 3 | $C_{16}H_{12}O_5$ | 67.4 | 4.4 | | | 67.6 | 4.3 | | |
| 4 | $C_{15}H_9ClO_4$ | 62.2 | 3.0 | | | 62.4 | 3.1 | | |
| 5 | $C_{16}H_{12}O_4$ | 71.6 | 4.8 | | | 71.6 | 4.5 | | |
| 6 | $C_{16}H_{12}O_5$ | 67.7 | 4.2 | | | 67.6 | 4.3 | | |
| 7 | $C_{15}H_9ClO_4$ | 62.2 | 2.9 | | 12.1 | 62.4 | 3.1 | | 12.3 |
| 8 | $C_{15}H_9ClO_4$ | 62.3 | 3.1 | | | 62.4 | 3.1 | | |
| 9 | $C_{16}H_{12}O_4$ | 71.5 | 4.4 | | | 71.6 | 4.5 | | |
| 10 | $C_{17}H_{14}O_4$ | 72.6 | 4.9 | | | 72.3 | 5.0 | | |
| 11 | $C_{21}H_{14}O_4$ | 76.7 | 4.1 | | | 76.4 | 4.3 | | |
| 12 | $C_{16}H_{12}O_5$ | 67.8 | 4.2 | | | 67.6 | 4.3 | | |
| 13 | $C_{17}H_{14}O_5$ | 68.5 | 4.8 | | | 68.4 | 4.7 | | |
| 14 | $C_{15}H_{10}O_5$ | 66.9 | 3.5 | | | 66.7 | 3.5 | | |
| 15 | $C_{15}H_9ClO_4$ | 62.3 | 2.9 | | 12.4 | 62.4 | 3.1 | | 12.3 |
| 16 | $C_{15}H_9NO_6$ | 59.8 | 2.9 | 4.8 | | 60.2 | 3.0 | 4.7 | |
| 17 | $C_{15}H_{11}NO_4$ | 66.6 | 4.0 | 5.2 | | 66.9 | 4.1 | 5.2 | |
| 18 | $C_{17}H_{13}NO_5$ | 65.3 | 4.2 | 4.6 | | 65.6 | 4.2 | 4.5 | |
| 19 | $C_{14}H_9NO_4$ | 65.7 | 3.4 | 5.5 | | 65.9 | 3.6 | 5.5 | |
| 20 | $C_{17}H_{12}O_6$ | 65.7 | 3.8 | | | 65.4 | 3.9 | | |
| 21 | $C_{18}H_{15}NO_5$ | 66.5 | 4.7 | 4.3 | | 66.5 | 4.7 | 4.3 | |
| 22 | $C_{16}H_{12}O_4$ | 71.7 | 4.4 | | | 71.6 | 4.5 | | |
| 23 | $C_{16}H_{12}O_5$ | 67.7 | 4.1 | | | 67.6 | 4.3 | | |
| 24 | $C_{15}H_{10}O_5$ | 66.6 | 3.6 | | | 66.7 | 3.7 | | |
| 25 | $C_{15}H_9ClO_4$ | 62.4 | 2.9 | | 12.3 | 62.4 | 3.1 | | 12.3 |
| 26 | $C_{16}H_{12}O_4$ | 71.3 | 4.5 | | | 71.6 | 4.5 | | |
| 27 | $C_{16}H_{12}O_5$ | 67.5 | 4.2 | | | 67.6 | 4.3 | | |
| 28 | $C_{15}H_{10}O_5$ | 66.9 | 3.5 | | | 66.7 | 3.7 | | |
| 29 | $C_{15}H_9ClO_4$ | 62.4 | 3.1 | | 12.2 | 62.4 | 3.1 | | 12.3 |
| 30 | $C_{15}H_9NO_6$ | 60.3 | 3.0 | 4.5 | | 60.2 | 3.0 | 4.7 | |
| 31 | $C_{16}H_{12}O_4$ | 71.6 | 4.4 | | | 71.6 | 4.5 | | |
| 32 | $C_{16}H_{12}O_5$ | 67.5 | 4.2 | | | 67.6 | 4.3 | | |
| 33 | $C_{15}H_9ClO_4$ | 62.7 | 3.2 | | | 62.4 | 3.1 | | |
| 34 | $C_{17}H_{14}O_4$ | 72.5 | 5.3 | | | 72.3 | 5.0 | | |
| 35 | $C_{19}H_{12}O_4$ | 74.9 | 3.8 | | | 75.0 | 4.0 | | |

TABLE II-continued
Elemental Analyses for the compounds of Table I

| No | Formula | Found C | H | N | Cl | Calculated C | H | N | Cl |
|---|---|---|---|---|---|---|---|---|---|
| 36 | $C_{19}O_{12}O_4$ | 74.8 | 3.7 | | | 75.0 | 4.0 | | |

The following Examples A–H illustrate the preparation of compounds of general formula (I).

EXAMPLE A

Preparation of compound 1 of Table I by Method 1a of Scheme I

A solution of 2-methylphenol (III: $R_3$=H) (33 g, 305 mmol) in MeOH (100 mL) was treated with Na (2.1 g, 90 mmol), and excess MeOH was removed under reduced pressure. Diphenyliodonium-2-carboxylate (II: $R_1$=H) (19.6 g, 60 mmol) and cupric acetate (0.5 g) were added and the mixture was stirred at 90° C. for 10 h. The solution was diluted with 2N NaOH, filtered through celite and acidified with HCl. The mixture was then dissolved in 2N $K_2CO_3$ and extracted twice with EtOAc to remove excess 2-methylphenol. The aqueous layer was then poured into excess 2N HCl to give 2-(2-methylphenoxy)benzoic acid (IV: $R_1$=$R_3$=H) (8.85 g, 64%), suitable for the next step. A sample crystallized from ligroin, mp 133°–134° C. (Ber, 1905, 38, 2111 records mp 133.5° C.).

The above acid (8.85 g, 39 mmol) was dissolved in polyphosphate ester (75 g) and heated at 100° C. until all volatiles were removed, and for a further 30 min. The mixture was diluted with an equal volume of MeOH and basified with $Na_2CO_3$. Addition of water then precipitated 4-methylxanthenone (VI: $R_1$=H, Z=$CH_3$), which was dried and crystallized from ligroin/ether to give needles (7.6 g, 93%), mp 124°–125° C. (Ber, 1905, 38, 2111 gives mp 126° C.).

A well-stirred mixture of the above 4-methylxanthenone (6.5 g, 31 mmol), N-bromosuccinimide (5.5 g, 31 mmol) and benzoyl peroxide (30 mg) in dry $CCl_4$ (250 mL) was heated under reflux with powerful illumination for 3 h. The hot mixture was filtered, the filtrate was evaporated and the residue was crystallized from the minimum volume of boiling petroleum ether (ca. 1800 mL) to give 4-bromomethylxanthenone (VII: $R_1$=H, Z=$CH_2Br$) (6.3 g, 71%) as colourless needles, mp 191°–192° C. Anal. ($C_{14}H_9BrO_2$) C,H,N,Br.

The above 4-bromomethylxanthenone (5.77 g, 20 mmol) was finely powdered and suspended in EtOH (150 mL). A hot solution of KCN (2.6 g, 40 mmol) in water (25 mL) was added, and the mixture was heated under reflux for 1 hour. A limited amount of hot water was then added to precipitate impurities which were removed by filtration. Further dilution with water then gave a crude product which was dried and crystallized from benzene-petroleum ether to give xanthenone-4-acetonitrile (VIII: $R_1$=H, Z=$CH_2CN$) (2.9 g, 62%). A sample crystallized from MeOH as prisms, mp 177°–178° C. Anal ($C_{15}H_9NO_2$) C,H,N.

The above acetonitrile (2.0 g) was dissolved in a mixture of AcOH (8 mL) and c.$H_2SO_4$ (8 mL), and heated under reflux for 90 min. Slow dilution with water gave a crystalline product, which was dissolved in warm aqueous $KHCO_3$. The solution was filtered and acidified with 2N HCl, and the resulting solid was crystallized from EtOH to give xanthenone-4-acetic acid (I; $R_1$=H) (1.6 g, 74%), mp 214°–216° C.

The water-soluble sodium salt was crystallized from MeOH-EtOAc.

EXAMPLE B

Preparation of compound 25 of Table I by Method 1b of Scheme I

A mixture of the sodium salts of 2,4-dichlorobenzoic acid (V: X=Cl, $R_1$=4-Cl) (27.7 g, 130 mmol) and 2-methylphenol (III: $R_3$=H) (18.9 g, 145 mmol) were dissolved in dry dioxan (300 mL). CuCl (1.3 g, 13 mmol) and tris-[2-(2-methoxyethoxy)ethyl]amine (TDA-1) (4.2 g, 13 mmol) were added, and the mixture was heated at reflux under $N_2$ for 8 hours. Excess solvent was evaporated under reduced pressure, and the residue was diluted with water and filtered. The filtrate was acidified with 2N HCl, and the resulting precipitate was collected, washed well with water and dried to yield 4-chloro-2-(2-methylphenoxy) benzoic acid (IV: $R_1$=4-Cl, $R_3$=H) (27 g, 79%), which was suitable for the next step. A sample was crystallized from aqueous MeOH as prisms, mp 158°–159° C. Anal. ($C_{14}H_{11}ClO_3$), C,H,Cl.

Similar reactions using appropriately substituted 2-halobenzoic acids (V and 2-methylphenols (III) gave the substituted 2-phenoxybenzoic acids (IV) listed in Table III wherein Z=$CH_3$.

The above crude acid (IV: $R_1$=4-Cl, $R_3$=H) was cyclized with polyphosphate ester as in Example A to give a 90% yield of 6-chloro-4-methylxanthenone (VI: $R_1$=6-Cl, Z=$CH_3$), mp (MeOH) 145°–146° C. Anal. ($C_{14}H_9ClO_2$) C,H,N.

Similar cyclization of related substituted 2-phenoxybenzoic acids (IV, Z=$CH_3$) with polyphosphate ester gave the substituted methylxanthenones (VI) listed in Table IV.

The above compound (VI: $R_1$=6-Cl; Z=$CH_3$) was then treated with N-bromosuccinimide as in Example A to give 4-bromomethyl-6-chloroxanthenone (VII: $R_1$=6-Cl, Z=$CH_2Br$), mp (benzene/petroleum ether) 217°–218° C. Anal. ($C_{14}H_8BrClO_2$) C, H,N.

Similar reaction of methylxanthenones listed in Table IV gave the corresponding substituted bromomethylxanthenones listed in Table IV.

Reaction of the above compound (VII: $R_1$=6-Cl, Z=$CH_2Br$) with KCN as in Example A gave 6-chloroxanthenone-4-acetonitrile (VIII: $R_1$=6-Cl, Z=$CH_2CN$), mp (MeOH) 193°–195° C. Anal. ($C_{15}H_8ClNO_2$) C,H,N.

Similar reaction of bromomethylxanthenones listed in Table IV gave the corresponding substituted xanthenoneacetonitriles listed in Table IV.

The above acetonitrile (VIII: $R_1$=6-Cl, Z=$CH_2CN$) was hydrolysed in acid as in Example A to give 6-chloroxanthenone-4-acetic acid (I: $R_1$=6-Cl), (compound 25 of Table I) mp (MeOH) 248°–249° C. Anal. ($C_{15}H_9ClO_4$) C,H,Cl.

The sodium salt was crystallized from MeOH-/EtOAc.

Similar reaction of xanthenone acetonitriles listed in Table IV gave the corresponding xanthenoneacetic acids listed in Table I.

This overall method was used to prepare compounds 4, 8, 9, 11, 12, 15, 19, 20, 23, 25, 27, 29, 33 and 35 of Table I.

TABLE III

Substituted 2-phenoxybenzoic acids (IV)

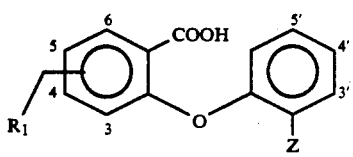

| $R_1$ | Z | Mp (°C.) | Formula | Analysis |
|---|---|---|---|---|
| 5'-CH$_3$ | CH$_2$COOH | 183–186 | C$_{16}$H$_{14}$O$_5$ | C, H |
| 5'-Cl | CH$_3$ | 116–118 | C$_{14}$H$_{11}$ClO$_3$ | C, H, Cl |
| 3'-Cl | CH$_3$ | 167–168 | literature[a] mp 168–169 | |
| 3'-NO$_2$ | CH$_3$ | 189–190 | literature[a] mp 187–190 | |
| 3-OCH$_3$ | CH$_2$COOH | 186–187 | C$_{16}$H$_{14}$O$_6$ | C, H |
| 3-Cl | CH$_3$ | 125–126 | C$_{14}$H$_{11}$ClO$_3$ | C, H, Cl |
| 3-NO$_2$ | CH$_2$COOH | 196–197 | C$_{15}$H$_{11}$NO$_7$ | C, H, N |
| 3-aza | CH$_3$ | 160–162 | C$_{13}$H$_{11}$NO$_3$ | C, H, N |
| 3-CH$_2$CH$_3$ | CH$_2$COOH | 151–153 | C$_{17}$H$_{16}$O$_5$ | C, H |
| 4-CH$_3$ | CH$_2$COOH | 209–211 | C$_{16}$H$_{14}$O$_5$ | C, H |
| 4-OCH$_3$ | CH$_3$ | 163.5–164.5 | C$_{15}$H$_{14}$O$_4$ | C, H |
| 5-OCH$_3$ | CH$_3$ | 132–133.5 | C$_{15}$H$_{14}$O$_4$ | C, H |
| 5-Cl | CH$_3$ | 125–126 | C$_{14}$H$_{11}$ClO$_3$ | C, H |
| 5-NO$_2$ | CH$_2$COOH | 244–246 | C$_{15}$H$_{11}$NO$_7$ | C, H, N |
| 3,4-diCH$_3$ | CH$_2$COOH | 240–242 | C$_{17}$H$_{16}$O$_5$ | C, H |
| 3,4-benz | CH$_2$COOH | 197–200 | C$_{19}$H$_{14}$O$_5$ | C, H |

Footnote for Table III
[a]P. Dure, P. Valenti, G. Primafiore & L. Cima, Chim. Ther., 1973, 60.

TABLE IV

Substituted xanthenones

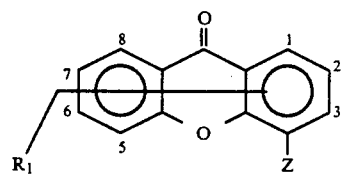

| $R_1$ | Z | Mp (°C.) | Formula | Analysis |
|---|---|---|---|---|
| 1-Cl | CH$_3$ | 130–133 | C$_{14}$H$_9$ClO$_2$ | C, H, Cl |
| 1-Cl | CH$_2$Br | 200–203 | C$_{14}$H$_8$BrClO$_2$ | C, H, Br |
| 1-Cl | CH$_2$CN | 182–185 | C$_{15}$H$_8$ClNO$_2$ | C, H, N |
| 3-Cl | CH$_3$ | 164–166 | literature[a] mp 163–164 | |
| 3-Cl | CH$_2$Br | 175–178 | literature[a] mp 186–188 | |
| 3-Cl | CH$_2$CN | 214–217 | C$_{15}$H$_8$ClNO$_2$ | C, H, N |
| 5-OCH$_3$ | CH$_3$ | 205–206 | C$_{15}$H$_{12}$O$_3$ | C, H |
| 5-OCH$_3$ | CH$_2$Br | 205–206 | C$_{15}$H$_{11}$BrO$_3$ | C, H, Br |
| 5-OCH$_3$ | CH$_2$CN | 202–203 | C$_{16}$H$_{11}$NO$_3$ | C, H, N |
| 5-Cl | CH$_3$ | 176–176.5 | C$_{14}$H$_9$ClO$_2$ | C, H |
| 5-Cl | CH$_2$Br | 181–182 | C$_{14}$H$_8$BrClO$_2$ | C, H, Br |
| 5-Cl | CH$_2$CN | 162–163 | C$_{15}$H$_8$ClNO$_2$ | C, H, N |
| 5-aza | CH$_3$ | 153–155 | C$_{13}$H$_9$NO$_2$ | C, H, N |
| 5-aza | CH$_2$Br | 214–216 | C$_{13}$H$_8$BrNO$_2$ | C, H, Br |
| 5-aza | CH$_2$CN | 200–201 | C$_{14}$H$_8$N$_2$O$_2$ | C, H, N |
| 5-CH$_2$Br | CH$_2$Br | 257–258 | C$_{15}$H$_{10}$BrO$_2$ | C, H, Br |
| 5-CH$_2$CN | CH$_2$Br | 257–259 | C$_{17}$H$_{10}$N$_2$O$_2$ | C, H, N |
| 5-Ph | CH$_3$ | 140–141 | C$_{20}$H$_{14}$O$_2$ | C, H |
| 5-Ph | CH$_2$Br | 184–185 | C$_{20}$H$_{13}$BrO$_2$ | C, H, Br |
| 5-Ph | CH$_2$CN | 178–179 | C$_{21}$H$_{13}$NO$_2$ | C, H, N |
| 6-OCH$_3$ | CH$_3$ | 151–152 | C$_{15}$H$_{12}$O$_3$ | C, H |
| 6-OCH$_3$ | CH$_2$Br | 179–180 | C$_{15}$H$_{11}$BrO$_3$ | C, H, Br |
| 6-OCH$_3$ | CH$_2$CN | 203–204 | C$_{16}$H$_{11}$NO$_3$ | C, H, N |
| 6-Cl | CH$_3$ | 145–146 | C$_{14}$H$_9$ClO$_2$ | C, H, Cl |
| 6-Cl | CH$_2$Br | 217–218 | C$_{14}$H$_8$BrClO$_2$ | C, H, Br |
| 6-Cl | CH$_2$CN | 193–195 | C$_{15}$H$_8$ClNO$_2$ | C, H, N |
| 7-OCH$_3$ | CH$_3$ | 123–124 | C$_{15}$H$_{12}$O$_3$ | C, H |
| 7-OCH$_3$ | CH$_2$Br | 183–185 | C$_{15}$H$_{11}$BrO$_3$ | C, H, Br |
| 7-OCH$_3$ | CH$_2$CN | 203–205 | C$_{16}$H$_{11}$NO$_3$ | C, H, N |
| 7-Cl | CH$_3$ | 143–145 | C$_{14}$H$_9$ClO$_2$ | |
| 7-Cl | CH$_2$Br | 200.5–201 | C$_{14}$H$_8$BrClO$_2$ | C, H, Br |
| 7-Cl | CH$_2$CN | 198–199 | C$_{15}$H$_8$ClNO$_2$ | C, H, N |

TABLE IV-continued

Substituted xanthenones

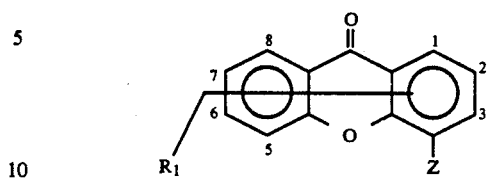

| $R_1$ | Z | Mp (°C.) | Formula | Analysis |
|---|---|---|---|---|
| 5,6-benz | CH$_3$ | 230–231 | C$_{18}$H$_{12}$O$_2$ | C, H |
| 5,6-benz | CH$_2$Br | 254–255 | C$_{18}$H$_{11}$BrO$_2$ | C, H, Br |
| 5,6-benz | CH$_2$CN | 221.5–222 | C$_{19}$H$_{11}$NO$_2$ | C, H, N |

Footnote for Table IV
[a]P. Dure, P. Valenti, G. Primafiore & L. Cima, Chim. Ther., 1973, 60.

EXAMPLE C

Preparation of compound 26 of Table I by Method 2a of Scheme II

2-[2-(Carboxymethyl)phenoxy]-5-methylbenzoic acid (XI: $R_1$=5-CH$_3$; $R_3$=H)

A mixture of 10 g (33 mmol) potassium 2-iodo-5-methylbenzoate, 7.8 g (40 mmol, 1.2 equiv.) disodium 2-oxidophenylacetate, 0.4 g (4 mmol) CuCl and 1.3 g (4 mmol) tris[2-(2-methoxyethoxy)ethyl]amine (TDA-1) in 150 ml dry dioxane was heated and stirred under reflux for 5 hours. The dioxane was removed under vacuum and the residue was dissolved in 100 ml 0.1N NaOH solution. After filtration to remove insoluble copper salts the solution was acidified with dilute hydrochloric acid and extracted with ethyl acetate. The organic layer was then extracted with dilute aqueous ammonia and the resulting aqueous solution was added slowly with stirring to dilute hydrochloric acid. The resulting precipitate was collected and dried to give 8.72 g (91% yield) of 2-[(2-carboxymethyl)phenoxy]-5-methylbenzoic acid (XI: $R_1$=5-CH$_3$, $R_3$=H). M.p. (ethyl acetate) 226°–227° C. Anal. (C$_{16}$H$_{14}$O$_5$) C,H.

Ring closure of the above compound with 90% H$_2$SO$_4$ gave an 87% yield of 7-methyl-xanthone-4-acetic acid (compound 26 of Table I)

Similar reactions using appropriately substituted 2-halobenzoic acids (V) and hydroxyphenylacetic acids (X) gave the phenoxyphenylacetic acids (IV) listed in Table III wherein Z=CH$_2$COOH (i.e. compounds of formula (XI)). Similar ring closure gave the corresponding xanthenone-4-acetic acids.

This method was used to prepare compounds 2, 10, 12, 13, 16, 22, 30, 31, 34, 35 and 36 of Table I.

EXAMPLE D

Preparation of compound 5 of Table I by the method of Scheme III (i) 4 Allyl-2-methylxanthenone (XIX; $R_1$=H; $R_3$=2-CH$_3$)

A mixture of 13.6 g (70 mmol) potassium 2-chlorobenzoate, 14.3 g (84 mmol, 1.2 equiv.) sodium 2-allyl-4-methylphenoxide, 0.8 g (8 mmol) CuCl and 2.6 g (8 mmol) tris[2-(2-methoxyethoxy)amine (TDA-1) in 200 ml anisole was heated and stirred under reflux for 3 hours. The anisole was removed under vacuum and the residue was extracted with dilute aqueous ammonia. After filtration to remove insoluble inorganics the aqueous solution was washed twice with ethyl acetate to remove remaining traces of anisole and excess 2-allyl-4- methylphenol. Acidification with conc. hydrochloric acid then gave an oil which was extracted into ethyl acetate. The organic layer was dried ($Na_2SO_4$) and the ethyl acetate was removed to give 10.6 g (47% yield) of crude 2-(2-allyl-4-methylphenoxy)benzoic acid (XVIII; $R_1$=H; $R_3$=4'-$CH_3$), as an oil. The oil was dissolved in 50 ml of a chloroform solution of polyphosphate ester (PPE) and heated on a waterbath with the solvent being allowed to boil off. After 30 min the residue was basified with dilute sodium hydroxide solution and the oil product was extracted into petroleum ether. After being dried ($Na_2SO_4$) the solvent was removed to give 6.5 g (66% yield) of 4-allyl-2-methylxanthenone (XIX: $R_1$=H; $R_3$=2-$CH_3$; m.p. (methanol) 97°-98° C. Anal. ($C_{17}H_{14}O_2$) C,H.

Similar reactions using appropriately substituted 2-allylphenoxides (XVII) gave the following compounds of formula (XVIII)

| $R_3$ | Z | Mp (°C.) | Formula | Analysis |
|---|---|---|---|---|
| 4'-$OCH_3$ | $CH_2CH=CH_2$ | 168-170 | $C_{17}H_{16}O_4$ | C,H |
| 4'-Cl | $CH_2CH=CH_2$ | 133-135 | $C_{16}H_{13}ClO_3$ | C,H | and then the following compounds of formula (XIX)

| $R_1$ | Z | Mp (°C.) | Formula | Analysis |
|---|---|---|---|---|
| 2-$OCH_3$ | $CH_2CH=CH_2$ | 109-112 | $C_{17}H_{14}O_3$ | C,H |
| 2-Cl | $CH_2CH=CH_2$ | 110-111 | $C_{16}H_{11}ClO_2$ | C,H |

(ii) 2-Methylxanthenone-4-acetic acid

A solution of 5 g (20 mmol) 4-allyl-2-methylxanthenone in a mixture of 75 ml acetic acid, 75 ml acetone and 50 ml water was cooled to below 5° C. and 15.8 g (5 equiv.) $KMnO_4$ was added in portions over 6 hours. After being stirred for a further 1 hour the mixture was poured into 1l of water and $Na_2S_2OS_n$ to remove $MnO_2$. The remaining solid was collected by filtration and dissolved in dilute aqueous ammonia solution. After treatment with charcoal and filtration through celite the clear solution was acidified with conc. hydrochloric acid to give 3.20 g (60% yield) of 2-methylxanthenone-4-acetic acid (compound 5 of Table I); m.p. (ethanol) 243°-245° C. Anal. ($C_{16}H_{12}O_4$) C,H.

Similar reaction of the other compounds of formula (XIX) listed above gave compounds 6 and 7 of Table I.

EXAMPLE E

Preparation of compound 11 of Table I by the method of Scheme IV

A mixture of 2-hydroxy-3-methylbenzoic acid (60.8 g 0.4 mol) 2-hydroxybiphenyl (68 g, 0.4 mol) and polyphosphate ester (Pollman and Schramm, Biochim, Biophys. Acta., 1964, 80, 1) (180 mL; used without solvent removal) was heated on a water bath with occasional swirling for 3 hours. Solvent still remaining after this time was removed in vacuo; the residue was poured on to crushed ice; excess powdered $NaHCO_3$ was added and then the mixture was stood at room temperature for 12 hours. The whole was extracted with $CH_2Cl_2$ (500 mL), filtered and the extract was washed with aqueous $NaHCO_3$ and then dried and evaporated. Extraction of the resulting oil with hot petroleum ether (b.p. 40°-60° C.) followed by solvent evaporation gave crude biphenyl ester (89 g, 73% yield) of sufficient purity (c.a. 85%) for use in the next stage.

Crude 2-biphenyl 2-hydroxy-3-methylbenzoate (78 g, c.a. 85% pure) was heated in a flask connected to a short distillation pathway to 280°-300° C. when a vigorous exotherm occurred resulting in rapid distillation of the pyrolysate. The highest bp fraction (340°-370° C. c.a. 26 g) was dissolved in boiling EtOH (300 mL), treated with 5N aqueous NaOH (60 mL), heated under reflux for 5 min and then the resulting solution was diluted with water. The solid which separated on cooling was collected, washed with water and recrystallised twice from petroleum ether (bp 80°-100° C.) (charcoal) to give pure 4-methyl-5-phenylxanthenone (XXIII: $R_1$=Ph) (8.8 g, 12% yield based on crude starting material) as colourless needles, m.p. 140°-141° C. Anal. ($C_{20}H_{14}O_2$) C,H.

This compound was then elaborated by the method outlined in Example A to give compound 11 of Table I.

EXAMPLE F

Preparation of compound of 9 of Table I

4-Bromomethyl-5-methylxanthenone

Powdered N-bromosuccinimide (5.0 g, 0.028 mol) was added to a warm solution of 4,5-dimethylxanthenone (prepared by the method of Schopff, Ber 1892, 25, 3642) in $CCl_4$ (170 mL) containing benzoyl peroxide (40 mg), and the mixture was stirred at reflux temperature under UV irradiation (illumination) for 3 hours. Removal of the solvent under reduced pressure gave a residue which was extracted with $CHCl_3$. The $CHCl_3$ layer was washed with cold 1N aqueous NaOH and water (twice), then dried and evaporated to give the crude product, contaminated with starting material and the 4,5-dibromomethylxanthenone. Repeated crystallization from benzene-petroleum ether gave pure material as colourless needles (1.96 g, 29%), m.p. 171°-172° C. Anal. ($C_{15}H_{11}BrO_2$) C,H,Br.

5-Methylxanthenone-4-acetonitrile

Powdered 4-bromomethylxanthenone (6.06 g, 0.02 mol) was added to a hot solution of NaCN (2.6 g, 0.04 mol) in water (30 mL) and EtOH (180 mL), and the mixture was stirred under reflux until homogenous and for a further 10 min. The hot solution was filtered and concentrated until separation of the product commenced. After cooling, the solid was collected and crystallized from EtOH to give the pure acetonitrile as prisms (3.1 g, 62%), mp 177°-178° C. Anal. ($C_{16}H_{11}NO_2$) C,H,N.

5-Methylxanthenone-4-acetic acid (compound 9 of Table I)

A mixture of the above acetonitrile (2.1 g), AcOH (8 mL), water (8 mL) and conc. $H_2SO_4$ (8 mL) was heated under reflux for 2 hours, then cooled and diluted with twice the volume of water. The resulting precipitate was collected, washed well with water, and extracted with warm dilute aqueous $KHCO_3$. The extract was clarified by filtration and acidified to give the desired product (2.08 g, 92%). Further crystallization from aqueous EtOH gave white prisms, mp 206°-208° C. Anal. ($C_{16}H_{12}O_4$) C,H. The sodium salt was crystallized from MeOH/EtOAc as prisms.

EXAMPLE G

Preparation of compound 2 of Table I by methods 2a and 2b of Scheme II

4-Methyl-2-phenylmethoxybenzoic acid (XII: $R_3$=4-$CH_3$)

A two-phase mixture of 45.6 g (0.3 mol) 4-methylsalicylic acid, NaOH (36 g, 0.9 mol), benzyl bromide (154 g, 0.9 mol) and tetrabutylammonium bromide (10 g, 30 mmol) in water (200 ml) and $CH_2Cl_2$ (200 ml) was stirred at room temperature for 3 hours. The layers were separated and the $CH_2Cl_2$ was removed from the organic fraction. The residue was dissolved in a mixture of ethanol (250 ml) and 2N NaOH (50 ml), and the mixture was heated under reflux for 30 min. The ethanol was removed under vacuum and the residue was diluted with water and washed with ethyl acetate. The aqueous layer was separated and acidified with dilute HCl to give a precipitate of 4-methyl-2-phenylmethoxybenzoic acid (65.3 g, 90%) m.p. (MeOH aq) 105°–107° C. Anal ($C_{15}H_{14}O_3$) C,H,O.

4-Methyl-2-phenylmethoxybenzenemethanol (XIII: $R_3=4$-$CH_3$, Z=OH)

A solution of 4-methyl-2-phenylmethoxy-benzoic acid (30.3 g, 0.125 mol) in 100 ml thionyl chloride containing 3 drops DMF was heated under reflux for 30 min. The $SOCl_2$ was removed under vacuum and the residual oil was diluted with 100 ml dry benzene. The solvent was again removed under vacuum to remove remaining traces of $SOCl_2$ and the crude acid chloride product was added slowly to a solution of $NaBH_4$ (10 g) in dry diglyme (200 ml) at 10°–20° C. The resulting mixture was stirred for 30 min at room temperature and the solvent was removed under vacuum by heating in an oilbath. Water (100 ml) was added slowly to the white solid and then acetic acid (10 ml) was added to ensure complete decomposition of the excess borohydride. The mixture was basified with conc. ammonia and extracted with ethyl acetate to give 4-methyl-2-phenylmethoxybenzenemethanol (26.6 g, 93% crude yield) as an oil.

1-Bromomethyl-4-methyl-2-phenylmethoxybenzene (XIV: $R_3=4$-$CH_3$, Z=Br)

A solution of crude 4-methyl-2-phenylmethoxy-benzenemethanol (20 g, 87.6 mmol) in dry benzene (100 ml) was treated with 9.1 ml (96 mmol) $PBr_3$ at room temperature and after being stirred for 10 min the mixture was treated with 50 ml 2N NaOH solution. The organic layer was separated and dried ($Na_2SO_4$) to give 1-bromomethyl-4-methyl-2-phenylmethoxybenzene (23.7 g, 93% crude yield) as an oil.

(4-Methyl-2-phenylmethoxyphenyl)acetonitrile (XV: $R_3=4$-$CH_3$, Z=CN)

A two-phase mixture of crude 1-bromomethyl-4-methyl-2-phenylmethoxybenzene (21.84 g, 75 mmol), NaCN (11.0 g, 0.22 mol), tetrabutylammonium bromide (2.4 g, 7.5 mmol), water (25 ml) and $CH_2Cl_2$ (50 ml) was stirred at room temperature for 1 hour and the layers were separated. The organic layer was washed well with water to remove tetrabutylammonium salts and after drying ($CaCl_2$) the solvent was removed to give (4-methyl-2-phenylmethoxyphenyl)acetonitrile (17.8 g, 100% crude yield) as an oil.

(2-Hydroxy-4-methylphenyl)acetic acid (X: $R_3=4$-$CH_3$)

A solution of crude 2-(4-methyl-2-phenylmethoxyphenyl)acetonitrile (15 g, 63 mmol) in ethanol (200 ml) and water (50 ml) containing 10 g (0.25 mol) NaOH was heated under reflux overnight, and the ethanol was removed under vacuum. The residue was diluted with water and washed with benzene. The aqueous layer was then acidified with dilute HCl to give an oil which was extracted into ethyl acetate to give (4-methyl-2-phenylmethoxyphenyl)acetic acid (14.2 g, 88%) as an oil which solidified on standing. A solution of this crude (4-methyl-2-phenylmethoxyphenyl)acetic acid in ethanol was hydrogenated over palladium on charcoal to give (2-hydroxy-4-methylphenyl)acetic acid. Anal ($C_9H_{10}O_3$) C,H.

2-[2-(Carboxymethyl)-5-methylphenoxy]benzoic acid (XI: $R_1=H$; $R_3=5'$-$CH_3$)

A mixture of potassium 2-chlorobenzoate (9.2 g, 47 mol), disodium 2-(4-methyl-2-oxide-phenyl)acetate (6.2 g, 29 mmol) (prepared from 4.9 g (2-hydroxy-4-methylphenyl) acetic acid and sodium hydroxide in methanol), CuCl (1g, 10 mmol) and tris[2-(2-methoxyethoxy)ethyl]amine (TDA-1) (3.2 g, 10 mmol) in dry dioxane (200 ml) was refluxed and stirred for 5 hours and the dioxane was removed under vacuum. The residue was dissolved in dilute ammonia solution and the solution was filtered. Acidification with conc. HCl gave the crude product which was extracted into ethyl acetate and washed with water. The product was extracted into dilute ammonia solution again and the resulting solution was poured slowly into dilute HCl to give a precipitate of [2-(carboxymethyl)-5-methylphenoxy]benzoic acid (4.70 g, 55%), m.p. (ethyl acetate) 183°–186° C. Anal ($C_{16}H_{14}O_5$).

Compound 2 of Table I

[2-(carboxymethyl)-5-methylphenoxy]benzoic acid (4 g, 14 mmol) was dissolved in a freshly prepared solution of conc. $H_2SO_4$ (80 ml) and water (20 ml) and after a further 5 min at >80° C. the mixture was poured into water. The solid was collected by filtration and washed with water and 50% aqueous methanol. Recrystallization from ethanol gave 1-methylxanthenone-4-acetic acid (3 g, 80%), m.p. 206°–209° C. Anal ($C_{16}H_{12}O_4$) C,H.

EXAMPLE H

Preparation of compound 28 of Table I

A suspension of 7-methoxyxanthenone-4-acetic acid (compound 27 of Table I) (2.0 g) in 48% w/w HBr (30 mL) was heated under reflux for 3 hours. The precipitate which formed on cooling was collected, washed with HBr and dissolved in aqueous $KHCO_3$. This solution was filtered and acidified with 2N HCl to give the crude product. Crystallization from MeOH gave pure compound 28 (1.51 g, 79%) as colourless needles, m.p. 232-234. Anal ($C_{15}H_{10}O_4$) C,H. Compounds 14 and 24 of Table I were prepared by similar methods from compounds 12 and 23, respectively, of Table I.

The compounds of general formula (I) have antitumour activity, as shown, for example, by the data given in Table V.

The cytotoxic activity of the compounds was measured in four different ways.

(1) Inhibition of growth of cultured cells

Mouse L1210 lymphocytic leukaemia cells were grown in RPM1 1640 medium supplemented with 10% foetal bovine serum, 50 um 2-mercaptoethanol, 100 units/ml penicillin and 100 ug/ml streptomycin as previously described (Baguley and Nash, Eur. J. Cancer, 17, 671–679, 1981). The toxic effect of xanthoneacetic acid derivatives was measured by exposure of the cells to the drug over a period of 70 hours. The $IC_{50}$ value is the drug concentration which reduces the cell number by 50% with respect to untreated cultures, and the following values (in $\mu M$) were determined:

Compound 1, >29 μM; 9, 16 μM; 25, 21 μM; 30, 29 μM.

Data for the other three assays is recorded in Table V.

(2) Activity against the P388 leukemia in mice

Mouse P388 leukemia cells were obtained as frozen cell stock from Mason Research Inc., USA, and were passaged intraperitoneally in DBA/25 mice of either sex, according to standard methods (Cancer Chemotherapy Reports, 1972, 3,9). Groups of six mice (F1 hybrids of DBA(2J male x C57 BL/6J female) were injected intraperitoneally with $10^6$ tumour cells on day 0. Antitumour activity was determined by published methods (Eur. J. Cancer, 19, 1607, 1983).

OD is the optimal drug dose (in milligrams per kilogram) administered intraperitoneally as a solution in 0.1 ml of 30% v/v ethyl alcohol/water on days 1, 5 and after tumour inoculation, the drug being given as a soluble basis addition salt.

$ILS_{max}$ is the percentage increase in lifespan of treated animals over that of control animals injected with tumour alone. The average survival of control mice was 11 days. ILS values greater than 20% are considered statistically significant.

NA implies no activity (3) Induction of haemorrhagic necrosis in Colon 38 tumours in mice Colon 38 tumour was obtained from Mason Research Inc. and passaged subcutaneously (sc) in C57BL/6J mice. Fragments (1 mm³ of an advanced sc tumour were inoculated sc into BDF1 (DBA/2J male x C57BL/6J female) mice and allowed to grow to a diameter of approximately 10 mM. Compounds were dissolved in H₂O and injected intraperitoneally. After 24 hours the tumour was removed surgically and fixed in 10% formaldehyde solution. Sections were made and stained with haematoxylin and eosin according to standard histological methods. Sections were examined by a histopathologist and scored as follows:

−: No evidence of toxic effects in comparison to untreated tumours (some areas of necrosis are usually observed in such tumours).

+: Evidence of cytopathological changes across the whole section.

++: Extensive haemorrhagic necrosis across the whole section.

(4) Induction of natural killer cell activity

BDF, hybrid mice (CS7 BL/6J×DBA/2J) were injected with drug intraperitoneally at the maximum tolerated dose. After 12 hours, spleen cells were collected and assayed for natural killer cell (NK) activity using the $^{51}Cr$ assay as published (Eur. J. Cancer Clin. Oncol., 1987, 23, 1047), and the results assessed as follows:

NA: not active

+: equal activity to flavoneacetic acid

++: higher activity than flavoneacetic acid

−: suppression of NK activity

Selected compounds were assayed for their ability to induce a delay in the growth of subcutaneous colon 38 tumours in mice, and these results are given in Table VI.

The colon 38 tumour was grown as above. Compounds were administered intraperitoneally in aqueous solution. Tumour diameters (major and minor axes) were measured twice weekly thereafter and calculated tumour volumes were compared to those of untreated control mice.

Under similar conditions the clinical agents, 5-fluorouracil (65 mg/Kg every 4 days×3) and cyclophosphamide (220 mg/Kg, single dose) provided no complete regressions and mean tumour growth delays of 10 and 4 days respectively.

TABLE V

| | Biological activity of the compounds of Table 1 | | | | | |
|---|---|---|---|---|---|---|
| | P388 in vivo | | colon 38 (histology) | | NK activity | |
| No | OD | ILS | OD | assessment | dose | assessment |
| 1 | | | 220 | ++ | 220 | + |
| 2 | | | 220 | + | | |
| 3 | | | 330 | ± | | |
| 4 | | | 330 | ± | | |
| 5 | | | 220 | ++ | 330 | − |
| 6 | | | 750 | + | 330 | − |
| 7 | | | 330 | ± | | |
| 8 | | | 220 | + | | |
| 9 | 45 | 30 | 45 | ++ | 45 | ++ |
| 10 | | | 150 | ++ | | |
| 11 | | | 220 | − | | |
| 12 | | | 150 | + | | |
| 13 | | | 330 | ++ | | |
| 14 | | | 330 | + | | |
| 15 | 65 | 34 | 100 | ++ | 100 | ++ |
| 16 | | | 150 | + | | |
| 17 | | | 500 | − | | |
| 18 | | | 500 | − | | |
| 19 | | | 500 | − | | |
| 20 | 150 | NA | 330 | − | 500 | NA |
| 21 | 225 | NA | 330 | − | | |
| 22 | | | 220 | ++ | 220 | + |
| 23 | 225 | NA | 150 | ++ | 150 | ++ |
| 24 | | | 500 | − | | |
| 25 | 150 | NA | 150 | ++ | 150 | + |
| 26 | | | 500 | + | | |
| 27 | 150 | NA | 330 | − | 330 | NA |
| 28 | | | 500 | ± | | |
| 29 | 225 | NA | 500 | − | 500 | NA |
| 30 | 225 | NA | 330 | − | 330 | NA |
| 31 | | | 330 | − | | |
| 32 | | | 330 | + | | |
| 33 | | | 750 | ± | | |
| 34 | | | 30 | ++ | | |
| 35 | | | 100 | ++ | | |
| 36 | | | 150 | ± | | |

TABLE VI

| | Growth delay of subcutaneous colon 38 tumours in vivo | | |
|---|---|---|---|
| compound | dose (mg/Kg) | schedule | growth delay (days) |
| 1 | 220 | 2 doses, 7 days apart | 11 |
| 9 | 45 | 2 doses, 7 days apart | 13 |
| 15 | 100 | single dose | 5.2 |
| 25 | 100 | single dose | 0 |

The results shown in Table V indicate that the compounds of formula (I) are useful as antitumour drugs, particularly against solid tumours, and also have potent immunostimulatory properties.

The present invention therefore also provides a compound of formula (I) or a pharmaceutically acceptable salt thereof, for use in the treatment of tumours and in particular tumours.

The present invention further provides pharmaceutical compositions having antitumour and/or immunostimulatory properties and comprising at least one compound of general formula (I) or a pharmaceutically acceptable salt thereof and one or more pharmaceutically acceptable carriers or diluents.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about 1 to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:

1. 5,6-dimethylxanthenone-4-acetic acid.
2. 5-methylxanthenone-4-acetic acid.
3. A method for treating tumours comprising administering in vivo an effective amount of a compound according to claim 1.

4. A method for treating tumours comprising administering in vivo an effective amount of a compound according to claim 2.

5. A pharmaceutical composition having antitumour activity which comprises a compound according to claim 1, or a pharmaceutically-acceptable basic addition salt thereof and one or more pharmaceutically acceptable carriers or diluents.

6. A pharmaceutical composition having antitumour activity which comprises a compound according to claim 2, or a pharmaceutically-acceptable basic addition salt thereof, or one or more pharmaceutically-acceptable carriers or diluents.

* * * * *